United States Patent [19]

Fauss et al.

[11] Patent Number: 4,659,821

[45] Date of Patent: Apr. 21, 1987

[54] PROCESS FOR THE PREPARATION OF 4-ALKOXY-6-ALKYL-2-CYANOAMINO-1,3,5-TRIAZINES

[75] Inventors: Rudolf Fauss, Cologne; Hans-Jochem Riebel, Wuppertal, both of Fed. Rep. of Germany

[73] Assignee: Bayer Aktiengesellschaft, Leverkusen, Fed. Rep. of Germany

[21] Appl. No.: 829,669

[22] Filed: Feb. 13, 1986

[30] Foreign Application Priority Data

Mar. 5, 1985 [DE] Fed. Rep. of Germany ....... 3507750

[51] Int. Cl.⁴ .......................................... C07D 251/16
[52] U.S. Cl. .................................................. 544/194
[58] Field of Search .......................... 544/194; 564/105

[56] References Cited

U.S. PATENT DOCUMENTS

1,611,941 12/1926 Osborne et al. ..................... 564/105
2,194,076 3/1940 Roblin, Jr. ........................... 564/105

FOREIGN PATENT DOCUMENTS

0121082 10/1984 European Pat. Off. .
2653834 6/1978 Fed. Rep. of Germany ...... 544/194
3334455 9/1984 Fed. Rep. of Germany .

Primary Examiner—Joseph Paul Brust
Attorney, Agent, or Firm—Sprung Horn Kramer & Woods

[57] ABSTRACT

A process for the preparation of a 4-alkoxy-6-alkyl-2-cyanoamino-1,3,5-triazine of the formula

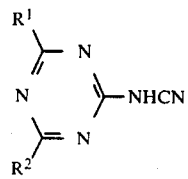

in which
$R^1$ is alkyl, and
$R^2$ is alkoxy, comprising reacting a 4-alkoxy-6-alkyl-2-amino-1,3,5-triazine of the formula

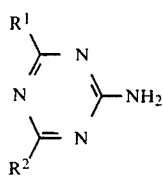

with a cyanogen halide of the formula

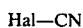

in which
Hal is halogen, in the presence of twice the molar amount of butyl-lithium and in the presence of a diluent adding water and acidifying.

2 Claims, No Drawings

PROCESS FOR THE PREPARATION OF 4-ALKOXY-6-ALKYL-2-CYANOAMINO-1,3,5-TRIAZINES

The present invention relates to a novel process for the preparation of 4-alkoxy-6-alkyl-2-cyanoamino-1,3,5-triazines, which can be used as intermediate products for the preparation of herbicides and plant growth regulators.

It is already known that 2-cyanoamino-1,3,5-triazines are obtained by reacting alkali metal or alkaline earth metal salts of cyanamide with the corresponding 2-halogeno-1,3,5-triazines. See U.S. Ser. No. 578,345 filed Feb. 9, 1984, now pending.

However, this process is only of very limited applicability because of the unsatisfactory methods for the preparation of the starting substances required. There is therefore a need for a new, widely applicable process for the preparation of 4-alkoxy-6-alkyl-2-cyanoamino-1,3,5-triazines.

It has now been found that 4-alkoxy-6-alkyl-2-cyanoamino-1,3,5-triazines of the general formula (I)

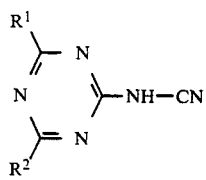

in which
$R^1$ represents alkyl and
$R^2$ represents alkoxy,
are obtained by a process in which 4-alkoxy-6-alkyl-2-amino-1,3,5-triazines of the formula (II)

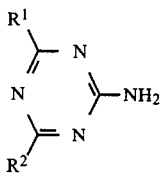

in which
$R^1$ and $R^2$ have the abovementioned meanings,
are reacted with cyanogen halides of the formula (III)

Hal—CN        (III)

in which
Hal represents halogen,
in the presence of twice the molar amount of butyl-lithium and in the presence of diluents, water is then added and the mixture is acidified.

Surprisingly, with this novel process, it is possible to obtain the compounds of the formula (I) in good yields. The yields are very unsatisfactory in the preparation of the compounds of the formula (I) in accordance with the prior art from alkali metal or alkaline earth metal salts of cyanamide and the corresponding halogeno-1,3,5-triazines. It was also not predictable that 2 moles of butyl-lithium have to be employed per mole of the starting substances (II) and (III); the use of 1 mole of butyl-lithium leads to a conversion of only 50%.

Compounds of the formula (I) which are preferably prepared with the aid of the process according to the invention are those in which
$R^1$ represents alkyl with 1 to 6 carbon atoms and
$R^2$ represents alkoxy with 1 to 6 carbon atoms.

Compounds of the formula (I) which are particularly preferably prepared are those in which
$R^1$ represents methyl, ethyl, n-propyl, i-propyl, n-butyl, i-butyl, sec.-butyl or tert.-butyl and
$R^2$ represents methoxy, ethoxy, n-propoxy, i-propoxy, n-butoxy, i-butoxy, sec.-butoxy or tert.-butoxy.

Compounds of the formula (I) which are especially preferably prepared are those in which
$R^1$ represents methyl, ethyl, n-propyl, i-propyl or n-butyl and
$R^2$ represents methoxy, ethoxy, n-propoxy, i-propoxy or n-butoxy.

If, for example, 2-amino-4-methoxy-6-methyl-1,3,5-triazine and cyanogen chloride are used as starting substances for the process according to the invention, the reaction can be represented by the following equation:

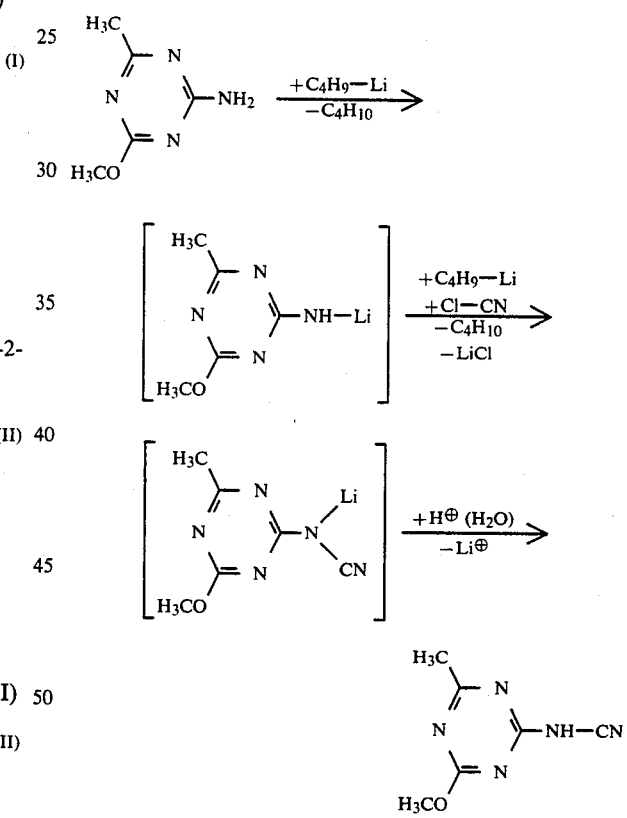

Formula (II) provides a general definition of the 4-alkoxy-6-alkyl-2-amino-1,3,5-triazines to be used as starting substances for the inventive process. In this formula, $R^1$ and $R^2$ preferably represent those radicals which are mentioned above as preferred or as particularly preferred in the context of the definition of the substituents of the formula (I).

Examples which may be mentioned of compounds of the formula (II) are: 6-methyl-4-methoxy-, 6-methyl-4-ethoxy-, 6-methyl-4-n-propoxy-, 6-methyl-4-i-propoxy-, 6-methyl-4-n-butoxy-, 6-methyl-4-i-butoxy-, 6-methyl-4-sec.-butoxy-, 6-methyl-4-tert.-butoxy-, 6-ethyl-4-methoxy-, 6-ethyl-4-ethoxy-, 6-ethyl-4-n-propoxy-, 6- ethyl-4-i-propoxy-, 6-ethyl-4-n-butoxy-, 6-ethyl-4-i-butoxy-, 6-ethyl-4-sec.-butoxy-, 6-ethyl-4-tert.-butoxy-, 6-n-propyl-4-methoxy-, 6-n-propyl-4-ethoxy-, 6-n-propyl-4-n-propoxy-, 6-n-propyl-4-i-propoxy-, 6-n-propyl-4-n-butoxy-, 6-n-propyl-4-i-butoxy-, 6-n-propyl-4-sec.-butoxy-, 6-n-propyl-4-tert.-butoxy-, 6-i-propyl-4-methoxy-, 6-i-propyl-4-ethoxy-, 6-i-propyl-4-n-propoxy-, 6-i-propyl-4-i-propoxy-, 6-i-propyl-4- n-butoxy-, 6-i-propyl-4-i-butoxy-, 6-i-propyl-4-sec.-butoxy-, 6-i-propyl-4-tert.-butoxy-, 6-n-butyl-4-methoxy-, 6-n-butyl-4-ethoxy-, 6-n-butyl-4-n-propoxy-, 6-n-butyl-4-i-propoxy-, 6-n-butyl-4-n-butoxy-, 6-n-butyl-4-i-butoxy-, 6-n-butyl-4-sec.-butoxy-, 6-n-butyl-4-tert.-butoxy-, 6-i-butyl-4-methoxy-, 6-i-butyl-4-ethoxy-, 6-i-butyl-4-n-propoxy-, 6-i-butyl-4-i-propoxy-, 6-i-butyl-4-n-butoxy-, 6-i-butyl-4-i-butoxy-, 6-i-butyl-4-sec.-butoxy-, 6-i-butyl-4-tert.-butoxy-, 6-sec.-butyl-4-methoxy-, 6-sec.-butyl-4-ethoxy-, 6-sec.-butyl-4-n-propoxy-, 6-sec.-butyl-4-i-propoxy-, 6-sec.-butyl-4-n-butoxy-, 6-sec.-butyl-4-i-butoxy-, 6-sec.-butyl-4-sec.-butoxy-, 6-sec.-butyl-4-tert.-butoxy-, 6-tert.-butyl-4-methoxy-, 6-tert.-butyl-4-ethoxy-, 6-tert.-butyl-4-n-propoxy-, 6-tert.-butyl-4-i-propoxy-, 6-tert.-butyl-4-n-butoxy-, 6-tert.-butyl-4-i-butoxy-, 6-tert.-butyl-4-sec.-butoxy- and 6-tert.-butyl-4-tert.-butoxy-2-amino-1,3,5-triazine.

The compounds of the formula (II) are known compounds of organic chemistry.

Formula (III) provides a general definition of the cyanogen halides also to be used as starting substances for the process according to the invention. In this formula, Hal represents halogen, preferably chlorine or bromine.

Examples which may be mentioned of the compounds of the formula (III) are: cyanogen chloride and cyanogen bromide.

The compounds of the formula (III) are generally known compounds of organic chemistry.

The process according to the invention is carried out in the presence of anhydrous, inert diluents. These include, in particular, aliphatic hydrocarbons, such as hexane, ethers, such as diethyl ether, dibutyl ether, glycol dimethyl ether, diglycol dimethyl ether, tetrahydrofuran and dioxane, amides, such as, for example, dimethylformamide, dimethylacetamide and N-methylpyrrolidone, and dimethylsulphoxide, tetramethylene sulphone and hexamethylphosphoric acid triamide.

The process according to the invention is in general carried out at temperatures between −20° C. and +60° C. The range between −10° C. and +40° C. is preferred. The reactions are in general carried out under normal pressure.

In carrying out the process according to the invention, a total of 2 moles of butyl-lithium and 1 mole of cyanogen halide of the formula (III) are employed per mole of the compound of the formula (II) and the mixture is then acidified with an acid, such as, for example, hydrochloric acid or acetic acid.

In carrying out the reaction, a procedure is in general followed in which an equimolar amount of butyl-lithium is added to a mixture of diluent and a compound of the formula (II) and, when the exothermic reaction has subsided, an equimolar amount of butyl-lithium and a solution of diluent and an equimolar amount of cyanogen halide of the formula (III) are simultaneously metered in.

After the reaction, the solvent is removed, water is added to the residue and the mixture is freed from the undissolved solid and acidified. The crystalline compounds of the formula (I) formed are filtered off with suction, recrystallised, if appropriate, and then dried.

The 4-alkoxy-6-alkyl-2-cyanoamino-1,3,5-triazines to be prepared by the process according to the invention can be employed as intermediate products for the preparation of guanidine derivatives which are active as herbicides and plant growth regulators (compare EP-OS (European Published Specification) No. 121,082).

PREPARATION EXAMPLES

Example 1

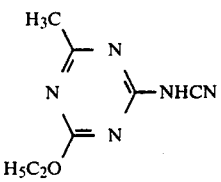

50 ml of an approximately 23% strength solution of butyl-lithium (0.115 mole) in hexane are added dropwise to a suspension of 17.7 g (0.115 mole) of 2-amino-4-ethoxy-6-methyl-1,3,5-triazine and 200 ml of tetrahydrofuran at 20° C. When the exothermic reaction has subsided, 50 ml of the approximately 23% strength solution of butyl-lithium (0.115 mole) in hexane and a solution of 5.9 ml (0.115 mole) of cyanogen chloride in 45 ml of tetrahydrofuran are simultaneously added dropwise to the reaction mixture at 15°–20° C. and the mixture is subsequently stirred at about 20° C. It is then concentrated and cold water is added. The residue is removed and the filtrate is acidified (pH value ≦4). The crystals formed are filtered off with suction and dried.

13.6 g (66% of theory) of 2-cyanamino-4-ethoxy-6-methyl-1,3,5-triazine, of melting point 192°–194° C. (decomposition), are obtained.

The following compound of the formula (I) is prepared analogously to Example 1:

Example 2

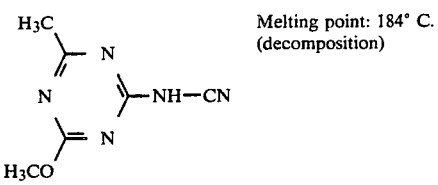

Melting point: 184° C. (decomposition)

It is understood that the specification and examples are illustrative but not limitative of the present invention and that other embodiments within the spirit and scope of the invention will suggest themselves to those skilled in the art.

We claim:

1. A process for the preparation of a 4-alkoxy-6-alkyl-2-cyanoamino-1,3,5-triazine of the formula

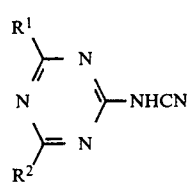

in which
  $R^1$ is alkyl with 1 to 6 carbon atoms, and
  $R^2$ is alkoxy, with 1 to 6 carbon atoms,
comprising reacting a 4-alkoxy-6-alkyl-2-amino-1,3,5-triazine of the formula

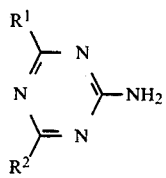

with a cyanogen halide of the formula

Hal—CN in which
  Hal is halogen,
in liquid phase at a temperature between −20° and +60° C. in the presence of twice the molar amount of butyl-lithium and in the presence of a diluent, adding water and acidifying.

2. The process according to claim 1, wherein one molar amount of butyl-lithium is first reacted and, when the exothermic reaction has subsided, the second molar amount of the butyl-lithium is added.

* * * * *